(12) United States Patent
Stewart et al.

(10) Patent No.: US 8,075,559 B2
(45) Date of Patent: Dec. 13, 2011

(54) APPARATUS AND METHOD FOR INTEGRATED VESSEL LIGATOR AND TRANSECTOR

(75) Inventors: Michael C. Stewart, San Jose, CA (US); Geoffrey H. Willis, Redwood City, CA (US); Joseph N. Lamberti, Castro Valley, CA (US); Charles J. Adam, San Jose, CA (US); Harry Ino, San Jose, CA (US); John P. Lunsford, San Carlos, CA (US)

(73) Assignee: Maquet Cardiovascular, LLC, San Jose, CA (US)

( * ) Notice: Subject to any disclaimer, the term of this patent is extended or adjusted under 35 U.S.C. 154(b) by 0 days.

(21) Appl. No.: 12/730,729

(22) Filed: Mar. 24, 2010

(65) Prior Publication Data

US 2010/0234843 A1 Sep. 16, 2010

Related U.S. Application Data

(63) Continuation of application No. 10/602,490, filed on Jun. 23, 2003, now Pat. No. 7,695,470, which is a continuation-in-part of application No. 10/455,942, filed on Jun. 6, 2003, now Pat. No. 7,534,243, which is a continuation-in-part of application No. 10/054,477, filed on Jan. 18, 2002, now Pat. No. 7,485,092, which is a continuation-in-part of application No. 09/413,012, filed on Oct. 5, 1999, now Pat. No. 7,938,842, which is a continuation of application No. 09/133,136, filed on Aug. 12, 1998.

(51) Int. Cl.
*A61B 18/18* (2006.01)

(52) U.S. Cl. .......................................... 606/51; 604/22
(58) Field of Classification Search .................. 606/159, 606/190, 49–51, 84; 604/22; 600/114, 206, 600/235
See application file for complete search history.

(56) References Cited

U.S. PATENT DOCUMENTS 2,004,559 A  6/1935  Wappler et al.
(Continued)

FOREIGN PATENT DOCUMENTS

DE  H24669  10/1956
(Continued)

OTHER PUBLICATIONS

Notice of Allowance dated Apr. 2, 2010 for U.S. Appl. No. 09/413,012.

*Primary Examiner* — Victor Nguyen
(74) *Attorney, Agent, or Firm* — Vista IP Law Group, LLP (57) ABSTRACT

Surgical treatment of tissue includes electro cauterization of blood vessels interposed between spaced sets of electrodes of opposite polarity, and includes transection of such tissue by a cutter that is mounted between the spaced sets of electrodes for translational and lateral movement relative to the sets of electrodes. Orientations of the sets of electrodes within a range of angles about an elongated axis of a supporting body are controlled by manual movement of an actuator mounted near a proximal end of the body for movement through a smaller range of angles via linkage connecting the actuator to the electrodes. Tissue dissection with gas insufflation to form an anatomical space in tissue is facilitated by a fluid outlet port located near the tissue-dissecting tip at the distal end of the elongated body that delivers through the tissue-dissecting tip to the dissected tissue a fluid under pressure that is supplied along a lumen within the elongated body.

22 Claims, 9 Drawing Sheets

U.S. PATENT DOCUMENTS

| | | | |
|---|---|---|---|
| 2,028,635 | A | 1/1936 | Wappler |
| 2,031,682 | A | 2/1936 | Wappler et al. |
| 3,200,028 | A | 8/1965 | Chisolm |
| 3,354,478 | A | 11/1967 | Allen |
| 3,391,690 | A | 7/1968 | Armao |
| 3,439,523 | A | 4/1969 | Wood |
| 3,613,682 | A | 10/1971 | Naylor |
| 3,625,202 | A | 12/1971 | Oyoshirhara et al. |
| 3,772,127 | A | 11/1973 | James |
| 3,929,137 | A | 12/1975 | Gonser |
| 3,934,115 | A | 1/1976 | Peterson |
| 3,938,527 | A | 2/1976 | Rioux et al. |
| 4,030,743 | A | 6/1977 | Warthen |
| 4,031,898 | A | 6/1977 | Hiltebrandt et al. |
| 4,196,734 | A | 4/1980 | Harris |
| 4,213,460 | A | 7/1980 | Weiner |
| 4,285,753 | A | 8/1981 | Warthen |
| 4,315,510 | A | 2/1982 | Kihn |
| 4,359,052 | A | 11/1982 | Staub |
| 4,370,980 | A | 2/1983 | Lottick |
| 4,493,320 | A | 1/1985 | Treat |
| 4,516,574 | A | 5/1985 | Hewes, Jr. |
| 4,597,379 | A | 7/1986 | Kihn et al. |
| 4,655,216 | A | 4/1987 | Tischer |
| 4,662,068 | A | 5/1987 | Polonsky |
| 4,671,274 | A | 6/1987 | Sorochenko |
| 4,705,041 | A | 11/1987 | Kim, II |
| 4,931,042 | A | 6/1990 | Holmes et al. |
| 4,979,771 | A | 12/1990 | Childs, III |
| 4,985,030 | A | 1/1991 | Melzer et al. |
| 5,007,898 | A | 4/1991 | Rosenbluth et al. |
| 5,046,251 | A | 9/1991 | Scott |
| 5,122,137 | A | 6/1992 | Lennox |
| 5,139,508 | A | 8/1992 | Kantrowitz et al. |
| 5,147,356 | A | 9/1992 | Bhatta |
| 5,151,102 | A | 9/1992 | Kamiyama et al. |
| 5,171,255 | A | 12/1992 | Rydell |
| 5,190,541 | A | 3/1993 | Abele et al. |
| 5,192,280 | A | 3/1993 | Parins |
| 5,197,649 | A | 3/1993 | Bessler et al. |
| 5,203,773 | A | 4/1993 | Green |
| 5,207,691 | A | 5/1993 | Nardella |
| 5,217,458 | A | 6/1993 | Parins |
| 5,226,890 | A | 7/1993 | Ianniruberto et al. |
| 5,226,908 | A | 7/1993 | Yoon |
| 5,250,046 | A | 10/1993 | Lee |
| 5,258,006 | A | 11/1993 | Rydell et al. |
| 5,267,998 | A | 12/1993 | Hagen |
| 5,276,306 | A | 1/1994 | Huffman |
| 5,279,565 | A | 1/1994 | Klein et al. |
| 5,290,249 | A | 3/1994 | Foster et al. |
| 5,290,286 | A | 3/1994 | Parins |
| 5,295,994 | A | 3/1994 | Bonutti |
| 5,330,497 | A | 7/1994 | Freitas et al. |
| 5,336,221 | A | 8/1994 | Anderson |
| 5,336,229 | A | 8/1994 | Noda |
| 5,346,504 | A | 9/1994 | Ortiz et al. |
| 5,352,222 | A | 10/1994 | Rydell |
| 5,360,428 | A | 11/1994 | Hutchinson, Jr. |
| 5,376,087 | A | 12/1994 | Haber et al. |
| 5,389,098 | A | 2/1995 | Tsuruta et al. |
| 5,401,273 | A | 3/1995 | Shippert |
| 5,403,312 | A | 4/1995 | Yates et al. |
| 5,411,508 | A | 5/1995 | Bessler et al. |
| 5,441,044 | A | 8/1995 | Tovey et al. |
| 5,443,463 | A | 8/1995 | Stern et al. |
| 5,445,638 | A | 8/1995 | Rydell et al. |
| 5,447,502 | A | 9/1995 | Haaga |
| 5,451,223 | A | 9/1995 | Ben-Simhon |
| 5,452,513 | A | 9/1995 | Zinnbauer et al. |
| 5,454,365 | A | 10/1995 | Bonutti |
| 5,458,598 | A | 10/1995 | Feinberg et al. |
| 5,480,409 | A | 1/1996 | Riza |
| 5,496,317 | A | 3/1996 | Goble et al. |
| 5,496,345 | A | 3/1996 | Kieturakis et al. |
| 5,512,721 | A | 4/1996 | Young et al. |
| 5,514,153 | A | 5/1996 | Bonutti |
| 5,514,236 | A | 5/1996 | Avellanet et al. |
| 5,527,331 | A | 6/1996 | Kresch et al. |
| 5,540,711 | A | 7/1996 | Kieturakis et al. |
| 5,556,563 | A | 9/1996 | von der Heyde et al. |
| 5,565,122 | A | 10/1996 | Zinnbauer et al. |
| 5,582,611 | A | 12/1996 | Tsuruta et al. |
| 5,591,183 | A | 1/1997 | Chin |
| 5,593,418 | A | 1/1997 | Mollenauer |
| 5,595,565 | A | 1/1997 | Treat et al. |
| 5,601,589 | A | 2/1997 | Forgarty et al. |
| 5,601,601 | A | 2/1997 | Tal et al. |
| 5,603,698 | A | 2/1997 | Roberts et al. |
| 5,607,441 | A | 3/1997 | Sierocuk et al. |
| 5,607,443 | A | 3/1997 | Kieturakis et al. |
| 5,647,871 | A | 7/1997 | Levine et al. |
| 5,653,726 | A | 8/1997 | Kieturakis |
| 5,665,085 | A | 9/1997 | Nardella |
| 5,667,520 | A | 9/1997 | Bonutti |
| 5,685,826 | A | 11/1997 | Bonutti |
| 5,688,270 | A | 11/1997 | Yates et al. |
| 5,688,286 | A | 11/1997 | Yoon |
| 5,690,847 | A | 11/1997 | LaValley et al. |
| 5,693,051 | A | 12/1997 | Schulze et al. |
| 5,702,417 | A | 12/1997 | Hermann |
| 5,707,382 | A | 1/1998 | Sierocuk et al. |
| 5,707,390 | A | 1/1998 | Bonutti |
| 5,709,680 | A | 1/1998 | Yates et al. |
| 5,716,325 | A | 2/1998 | Bonutti |
| 5,720,763 | A | 2/1998 | Tovey |
| 5,722,934 | A | 3/1998 | Knight et al. |
| 5,725,479 | A | 3/1998 | Knight et al. |
| 5,730,756 | A | 3/1998 | Kieturakis et al. |
| 5,735,848 | A | 4/1998 | Yates et al. |
| 5,738,628 | A | 4/1998 | Sierocuk et al. |
| 5,755,717 | A | 5/1998 | Yates et al. |
| 5,776,112 | A | 7/1998 | Stephens et al. |
| 5,797,907 | A | 8/1998 | Clement |
| 5,807,393 | A | 9/1998 | Williamson, IV et al. |
| 5,810,811 | A | 9/1998 | Yates et al. |
| 5,817,061 | A | 10/1998 | Goodwin et al. |
| 5,817,062 | A | 10/1998 | Flom et al. |
| 5,827,279 | A | 10/1998 | Hughett et al. |
| 5,827,281 | A | 10/1998 | Levin |
| 5,827,318 | A | 10/1998 | Bonutti |
| 5,843,017 | A | 12/1998 | Yoon |
| 5,860,997 | A | 1/1999 | Bonutti |
| 5,868,785 | A | 2/1999 | Tal et al. |
| 5,871,498 | A | 2/1999 | Jervis et al. |
| 5,873,889 | A | 2/1999 | Chin |
| 5,914,062 | A | 6/1999 | von der Heyde |
| 5,944,732 | A | 8/1999 | Raulerson et al. |
| 5,976,130 | A | 11/1999 | McBrayer et al. |
| 5,980,549 | A | 11/1999 | Chin |
| 6,015,423 | A | 1/2000 | Andrese |
| 6,077,277 | A | 6/2000 | Mollenauer et al. |
| 6,176,825 | B1 | 1/2001 | Chin et al. |
| 6,287,304 | B1 | 9/2001 | Eggers et al. |
| 6,432,115 | B1 | 8/2002 | Mollenauer et al. |
| 6,544,260 | B1 | 4/2003 | Markel et al. |
| 6,811,546 | B1 | 11/2004 | Callas et al. |
| 6,951,568 | B1 | 10/2005 | Chin |
| 2004/0102804 | A1 | 5/2004 | Chin |

FOREIGN PATENT DOCUMENTS

| | | |
|---|---|---|
| DE | 2550693 | 5/1977 |
| DE | 3002088 | 7/1981 |
| DE | 40469 | 8/1987 |
| EP | 517244 A1 | 12/1992 |
| EP | 518230 | 12/1992 |
| EP | 517244 B1 | 3/1996 |
| EP | 0878168 | 11/1998 |
| SU | 639545 | 12/1987 |
| SU | 1498474 | 8/1989 |
| WO | 92/08513 | 5/1992 |
| WO | 93/08754 | 5/1993 |
| WO | 94/24949 | 11/1994 |
| WO | 94/24951 | 11/1994 |
| WO | 98/38935 | 9/1998 |

APPARATUS AND METHOD FOR INTEGRATED VESSEL LIGATOR AND TRANSECTOR

RELATED APPLICATIONS

This application is a continuation of U.S. patent application Ser. No. 10/602,490, filed on Jun. 23, 2003, which is a continuation-in-part of U.S. patent application Ser. No. 10/455,942, filed on Jun. 6, 2003, issued as U.S. Pat. No. 7,534,243 on May 19, 2009, which is a continuation-in-part of U.S. patent application Ser. No. 10/054,477, filed on Jan. 18, 2002, issued as U.S. Pat. No. 7,485,092 on Feb. 3, 2009, which is a continuation-in-part of U.S. Pat. application Ser. No. 09/413,012, filed on Oct. 5, 1999, which is a continuation of U.S. patent application Ser. No. 09/133,136, filed on Aug. 12, 1998, the entire disclosures of all of which are expressly incorporated by reference.

FIELD OF THE INVENTION

This invention relates to tissue transectors, and more particularly to such devices having electrocautery electrodes disposed for selective cauterization and captivating of tissue structures such as blood vessels during surgical procedures to hemostatically seal and transect the vessels.

BACKGROUND OF THE INVENTION

Endoscopic surgery commonly requires manual manipulation of surgical instruments that are introduced into a surgical site within a patient through elongated cannulas containing one or more interior lumens of slender cross section. Endoscopic surgery to harvest a vessel such as the saphenous vein or the radial artery usually involves an elongated cannula that is advanced along the course of the vein from an initial incision to form an anatomical space about the vein as connective tissue is dissected away from the vein.

Lateral branch vessels of the saphenous vein can be conveniently isolated and ligated within the anatomical space under endoscopic visualization using surgical scissors that can be positioned and manipulated through the elongated cannula. Such surgical procedures are commonly employed in the preparation of the saphenous vein for removal from within the anatomical space for use, for example, as a shunting or graft vessel in coronary bypass surgery.

Surgical scissors that are used to transect vessels within the confines of limited anatomical space formed along the course of the saphenous vein commonly incorporate electrodes on or near the tissue-shearing blades. Scissors of this type are suitable for monopolar or bipolar electro cauterization of tissue prior to transection of, for example, lateral side branches of the saphenous vein to be harvested. However, placement of the electrodes in relation to the tissue-shearing edges of the scissor blades may inhibit proper operation of the scissor blades to shear tissue and may inhibit thorough electro cauterization of a side branch vessel as the scissor blades close during transection of the vessel.

Additionally, the scissor blades are conventionally rotated about a common pivot axis at the distal end of an elongated body using actuating levers within confined dimensions to preserve the diminutive sectional area of the scissors suitable for passage through a lumen of an elongated cannula. The associated linkage to a manual actuator at the proximal end of the elongated body commonly establishes little mechanical advantage sufficient for remotely shearing tissue under control of the proximal actuator, with resultant jamming of the scissor blades or other impediments to orderly surgical procedures. Additionally, repeated opening and closing of the scissor blades is a tedious procedure required to slice tissue along an extended path.

Subcutaneous tissue-dissecting procedures are commonly performed under visualization through an endoscope that is positioned within a cannula and that is protected from directly contacting the tissue by a tapered transparent tip that performs the dissection as the assembly is advanced through tissue. The dissected tissue may also be dilated by insufflating the anatomical space formed in the dissected tissue using gas under pressure that is supplied to the dissected anatomical space, usually through an access port located at the initial cutaneous incision where tissue dissection begins. However, visualization through the transparent tip of the tissue being dissected is commonly obscured by tissue and bodily fluids that contact the tip. In addition, insufflating an anatomical space via gas introduced under pressure through the access port becomes more problematic as the anatomical space is extended remotely from the access port and the dissected tissue surrounds the dissecting instrument. It would be desirable to overcome remote tissue-cutting difficulties, and to provide reliable visualization through a transparent tip during tissue dissection to form an anatomical space in tissue while under insufflation.

SUMMARY OF THE INVENTION

In accordance with the illustrated embodiment of the present invention, a tissue transector includes a pair of yoke-like electrodes mounted in spaced, substantially parallel relationship at the distal end of a slender, flexible body for manual extension and rotational orientation under control of a lever mounted at the proximal end of the slender body. The electrodes are positioned to supply electrical energy from an external source to cauterize tissue positioned between the yokes prior to shearing the cauterized tissue via a slicing blade at a remote surgical site in a patient. The transector may be angularly positioned about the elongated axis of the body to orient the yoke-like electrodes for effective electro cauterization of the tissue to be sheared within a wide range of angular orientations about the elongated axis of the body. In one embodiment, the slicing blade is interposed between a pair of spaced yoke-like electrodes to slice tissue traversing the electrodes using a translational movement that retracts the slicing blade into the body while passing through the tissue. The electrodes may be angularly oriented about the elongated axis of the body under manual control of an actuator mounted at the proximal end of the body for angular and translational movements linked to the electrodes and slicing blade mounted at the distal end of the body.

In another embodiment of the invention, a tissue-shearing blade is mounted on the transparent tissue-dissecting tip to facilitate transecting tissue within the endoscopic field of visualization. One or more of the embodiments of the present invention may be incorporated into and form an integral part of more comprehensive surgical apparatus, for example, as illustrated and described with reference FIGS. 8 and 9 of pending application Ser. No. 10/054,477, entitled "Vessel Harvesting Apparatus and Method", filed on Jan. 18, 2002 by M. Stewart et al.

DETAILED DESCRIPTION OF THE INVENTION

Figure 1:
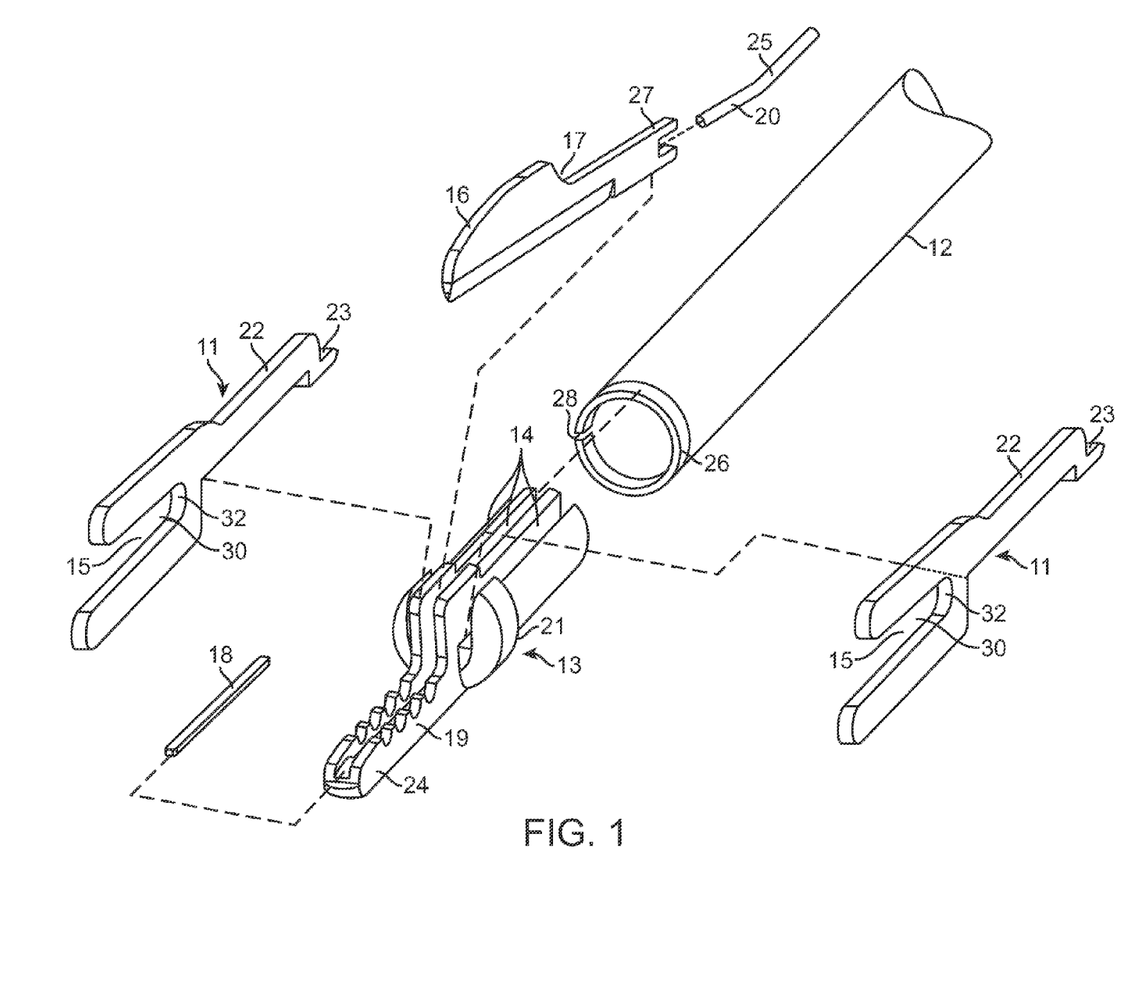
FIG. 1 is an exploded perspective view of one embodiment of the tissue transector according to the present invention.
Figure 2A:
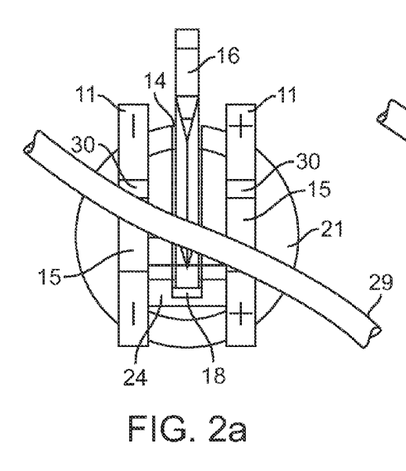
FIGS. 2a and 2b are end views of the tissue transector of FIG. 1.
Figure 2B:
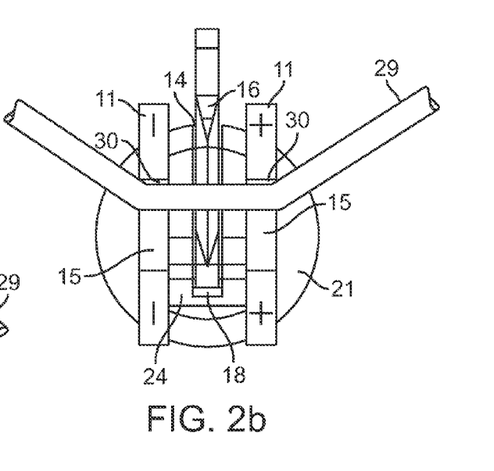

Referring now to the exploded perspective view of FIG. 1, there is shown the distal end of an elongated hollow support body 12 for the tissue electrocauterizer and transector in accordance with one embodiment of an end effector of the present invention. An electrically-insulating hub 13 formed of a polymer such as polycarbonate is disposed to fit within the internal bore of the body 12, up to the axial extent of a flange 21 surrounding the perimeter of the hub 13 at about the mid-length thereof. The hub 13 includes three spaced, parallel slots 14 that are vertically aligned to receive therein a tissue-slicing blade 16 in the central slot and two yoke-shaped planar electrodes 11 in the slots 14 disposed on opposite sides of the central slot. Each of the electrodes 11 includes an axially-aligned recess or slot 15 having a width that may taper inwardly 30 from a forward edge of the electrode, as shown in FIGS. 2a, 2b, or that may be substantially uniform in width along the length thereof. Each of the electrodes has a rearward portion 22 that is integral with the forward yoke-shaped portion, and that fits within the corresponding slot 14 of the hub 13 for holding the electrode firmly therein with the hub 13 positioned within the bore of the electrically insulating distal end of body 12. The base or root 32 of the slot 15 extends forward of the adjacent hub to promote electrical contact thereat with vessels of smallest diameter received into the slots 15. Each electrode 11 includes a connector tab 23 for attachment thereto of an electrical conductor (not shown) for supplying electrocautery signal thereto, as later described herein, with common polarity oriented in spaced planes that are substantially normal to a vessel disposed between slots 15 in the pair of electrodes.

The insulating hub 13 also includes a forward jaw-like portion 24 that substantially aligns with the lower branches of the yoke-shaped electrodes 11, and that includes an axial slot therein that extends in alignment with the central slot 14 through the rearward portion of the hub 13. The base of the forward portion of the central slot may be fitted with a strip 18 of metal or preferably Tecothane™ in the forward portion 24 to serve as an anvil for the blade 16. The upper edges of the forward portion of the central slot include serrations or upwardly-oriented 'teeth' 19 to aid in holding tissue in position within the recesses 15 of the adjacent electrodes 11 during tissue-cutting operation. The 'teeth' 19 may protrude slightly into the width of the recesses 15 in the adjacent electrodes 11 to facilitate holding tissue being cauterized or cut.

Specifically, tissue disposed within the recess 15 of the electrodes may be electrocauterized, as described later herein, and transected by the slicing movement of the blade 16 that translates and elevates within the central slot 14 in hub 13. The blade 16 is securely attached to an actuating rod 20 that controls simultaneous elevation and translation of the blade 16 within the central slot 14. The actuator rod 20 includes a resilient bend 25 proximal to the attachment of the blade 16 to the rod 20 for resiliently biasing the top edge 17, 27 of the rear portion of the blade against the top edge of the bore in tube 12 at the distal end thereof. A ferrule or ring 26 of wear-resistant material such as metal or dense polymer may be fitted at the distal end of tube 12 to inhibit wear during sliding contact with the top edge 17, 27 of the blade 16. The ring 26 may be split 28 to provide variable spacing and resilient force of the blade 16 against the anvil 18. Thus, forward extension of the blade 16 configures the assembly in an 'open' position relative to the anvil 18 at the base of the central slot 14. As the rod 20 is retracted proximally within the bore of body 12, the upper edge 17, 27 of the blade 16 is engaged with the distal upper edge of the body 12 and ring 26. Additionally, the inclined portion 17 of the upper edge engages the distal upper edge of the body 12 and ring 26 to reduce the elevation of the cutting edge of blade 16 relative to the anvil 18 toward a 'closed' configuration. Thus, translational or axial movement of the rod 20 in the proximal direction produces a compound slicing and closing movement of the blade 16 within the central slot relative to the forward portion 24 of the hub 13 that supports the anvil 18 for blade 16. Tissue disposed within the recesses 15 of the electrodes above the serrations 19 is thus transected in a smooth, slicing movement of the blade 16 as the rod 20 is selectively moved proximally, in the manner as described herein. The resilient biasing force provided by the ring 26 in the direction to urge the blade 16 into the anvil 24 may be altered by modifying the width or thickness or material of the ring in known manner, or by altering the angular orientation of the split 28 about the axis of the body 12.

Referring now to FIGS. 2a and 2b, there are shown end views of the transector of FIG. 1, with illustrative engagements of the yoke-like electrodes 11 and a tissue structure such as a blood vessel 29. Electro cauterization may be achieved by engaging the tissue structure 29 within the recesses or slots 15 of the yoke-shaped electrodes 11, and energizing the electrodes, for example, in the bipolar manner of opposite polarities of direct current or instantaneous polarities of alternating current, as shown. The yoke-shaped electrodes 11 facilitate establishing good electrical contact with the tissue structure 29, despite relative orientations thereof such as in diagonal traversal between upper tine of one yoke and lower tine of the other yoke, as shown in FIG. 2a, or in lateral traversal between corresponding tines of the two yokes, as shown in FIG. 2b, or in maximum insertion to the root or base of slots 15. Of course, the electrodes 11 may also be energized in unipolar manner (of one/same polarity) relative to a patient's grounded body, or relative to a grounded blade 15 brought into contact with a tissue structure 29, in the manner as previously described herein.

Following electro cauterization of a tissue structure 29, the actuator rod 20 is tensioned proximally to retract the blade 16 into the bore within the body 12, and simultaneously to advance the cutting edge of the blade 16 toward the 'closed' configuration against the anvil 18, as previously described. These movements promote smooth slicing action through the tissue structure 29 that tends to be further drawn into the recesses 15 in the spaced electrodes 11 and down onto the serrations 19 on the upper edges of the forward portion 24 of the hub 13 disposed between the electrodes 11 for secure anchoring of the tissue structure 29 during transection in this manner. Additionally, tissue structures 29 of larger sectional dimensions may be wedged into tapered recesses 15 in the yoke-like electrodes 11 for enhanced electrical connection thereto during electro cauterization, and for improved anchoring during transection.

Figure 2C:
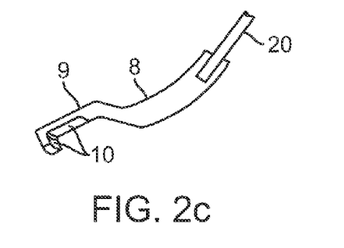
FIG. 2c is a perspective view of an alternative configuration of a blade for the embodiment of FIG. 1.

Alternatively, the blade 16 may be positioned substantially as illustrated in FIGS. 2a and 2b with the cutting edge of the blade 16 angled downwardly and inwardly across the dimensions of the slots 15 to facilitate slicing sheet-like tissue structures by simply advancing the structure through the sheet-like tissue, without moving the blade between open and closed configurations. Alternatively, as illustrated in the perspective view of FIG. 2c, a tissue-cutting blade 9 may include an angled or 'hook'-shaped sharpened edge 10 that may be retracted in a proximal direction to anchor a target vessel within the slots 15 in electrodes 11, and to sever the vessel during translational, retracting movement relative to the electrodes 11. A camming upper edge 8 of the blade 9 may curve upwardly from the rearward or proximal end of the blade 9 to facilitate camming action against a reference edge such as ring 26 and to increase the upward movement into the 'open' configuration via reduced translational movement.

Figure 2D:
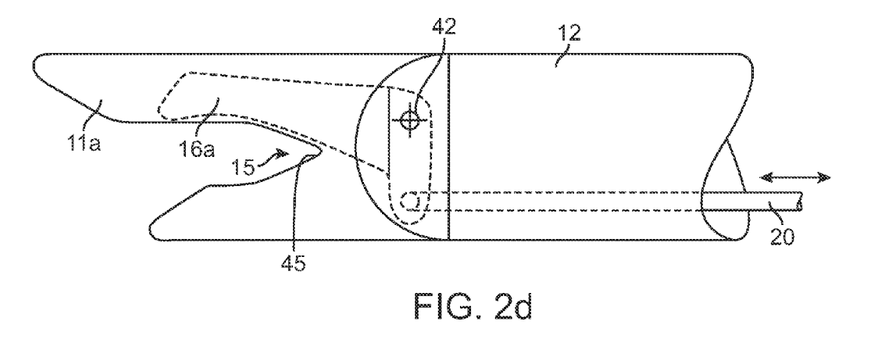
FIG. 2d is a partial side sectional view of another embodiment of a tissue transector according to the present invention.

As illustrated in the partial side sectional view of FIG. 2d, the upper and lower tines of each of the electrodes 11 may be shaped asymmetrically, with longer, broader tines 11a adjacently arranged and disposed to confine a blade 16a therebetween. The blade 16a is pivotally mounted to rotate about an anchored pivot 42 in response to translational movement of the actuator rod 20 that is linked thereto. The slots 15 in the electrodes may taper to a cusp or apex 45 to assure wedged engagement of a target vessel within the transversely-aligned slots 15 for promoting good electrical contact with the vessel.

In accordance with an embodiment of the present invention, the elongated hollow support body 12 (or the hub 13 alone) may be angularly oriented over a range of angles about the axis of the elongated body to facilitate easy alignment and engagement of the recesses 15 in the electrodes 11 with the random orientations of tissue structures 29 encountered during a surgical procedure. Specifically, as illustrated pictorially in FIGS. 3a, 3b, a finger-engageable control element 31 is mounted for rotation about an axis 36 aligned with the elongated axis of the body 13, and is mechanically linked to a connecting member 34 that is mounted for rotation about an axis 35 at a shorter radius to the link 33 than the radius of the control element 31 to its rotational axis 36. The link 33 includes a slot 37 in one of the control element 31 and connecting member 34 in which a pin of the link 33 attached to the other of the control element 31 and connecting member 34 may slide to take up the differential variation in distances to the respective rotational axes 35, 36 as the control element 31 and connecting member 34 rotate in response to manual movement of the control element 31. In this way, the connecting member 34 attached to the body 12 (or to the hub 13 alone) may rotate through a greater range of angles, α, for a smaller range of angular movement, β, of the control element 31.

Figure 3A:
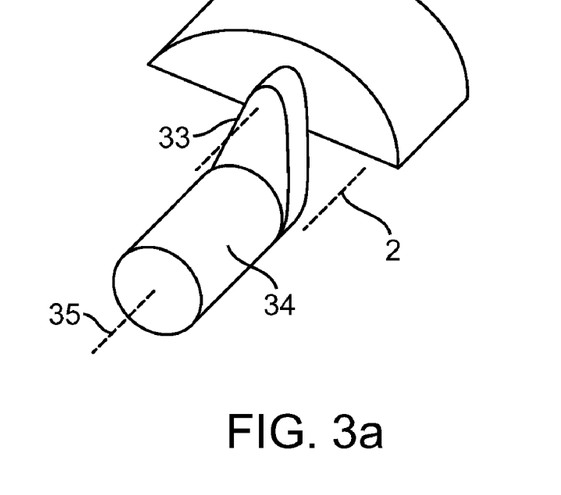
FIG. 3a is an exploded perspective view of a manual manipulator for the transector of FIG. 1.
Figure 3B:
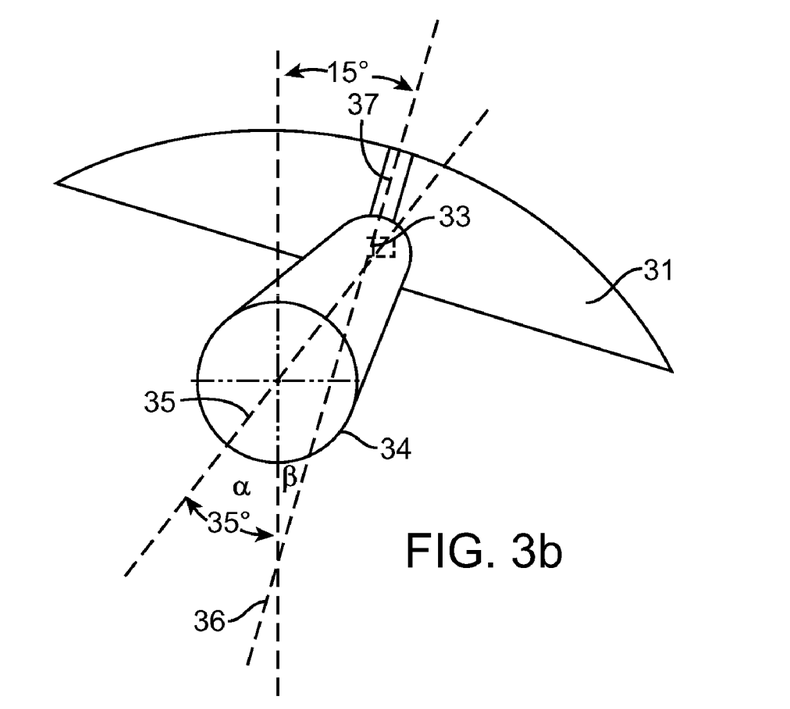
FIG. 3b is an end view of the manipulator of FIG. 3a illustrating the mechanical characteristics thereof.

In addition, the control element 31 may also control deployment and retraction of the hub 13 and electrodes 11 and blade 16 for convenient manual operation from the proximal end of the body 12.

Figure 3C:
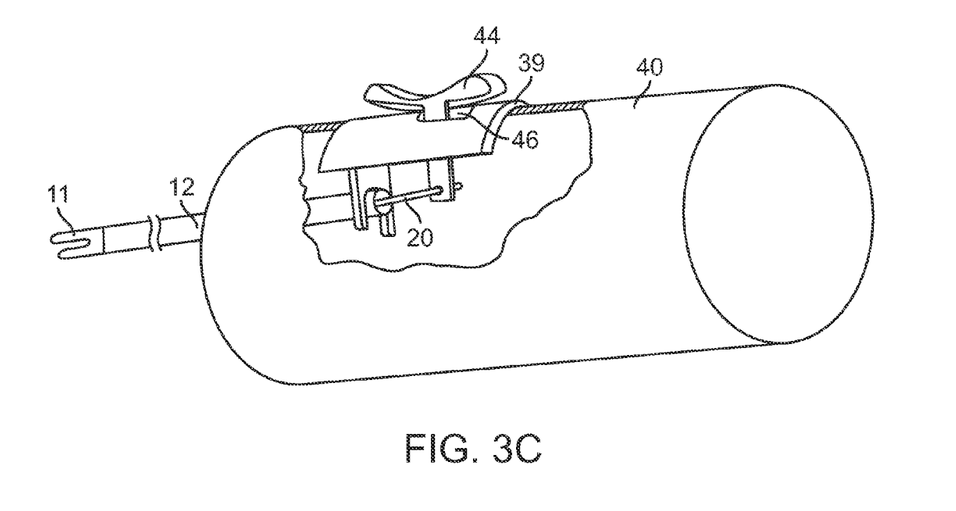
FIG. 3c is a perspective view of one embodiment of a manual manipulator for the transector of FIG. 1.

In one embodiment, as illustrated in the perspective view of FIG. 3c, the manual control element may include a first member 39 that is mounted to slide fore and aft along the longitudinal axis of a proximal handle 40 and that is coupled to the body 12 for selectively advancing and retracting the body relative to the handle 40. The manual control element may also include a second member 44 that is mounted for longitudinal movement within an elongated longitudinal slot 46 in the first member, and that is coupled to the rod 20 for selectively advancing and retracting the rod 20 and attached blade 16 relative to the body 12 and electrodes 11. Thus, the electrodes 11 and blade 16 may be selectively advanced, with blade 16 in the open position, as the second member 44 is advanced distally to the extent of the slot 46. Proximal movement of the second member 44 within the slot 46 actuates the blade 16 into the closed position across the transverse spacing of the aligned slots 15 in the electrodes 11 (as to sever tissue disposed therein), in the manner as previously described herein. Then, continuous proximal movement of the second member 44 against the proximal limit of the slot 46 also slides the first member 39 proximally to facilitate retraction of the electrodes 11 during one continuous movement of the second member 44 over a length of travel in excess of the length of slot 46.

Figure 4:
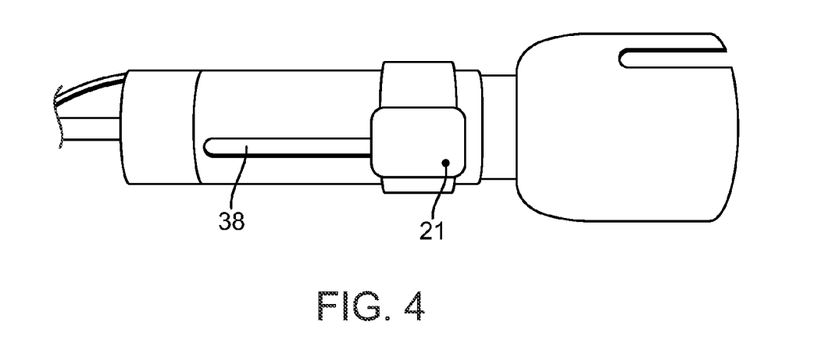
FIG. 4 is a plan view of an embodiment of a manual manipulator for the transector of FIG. 1.

Referring now to the plan view of FIG. 4, there is shown one embodiment of the present invention including a control element 31 disposed to rotate about a barrel segment of a proximal handle, and to translate along slot 38 in the barrel for deploying and retracting the electrodes 11 and blade 16 in a manner as previously described herein.

Figure 5A:
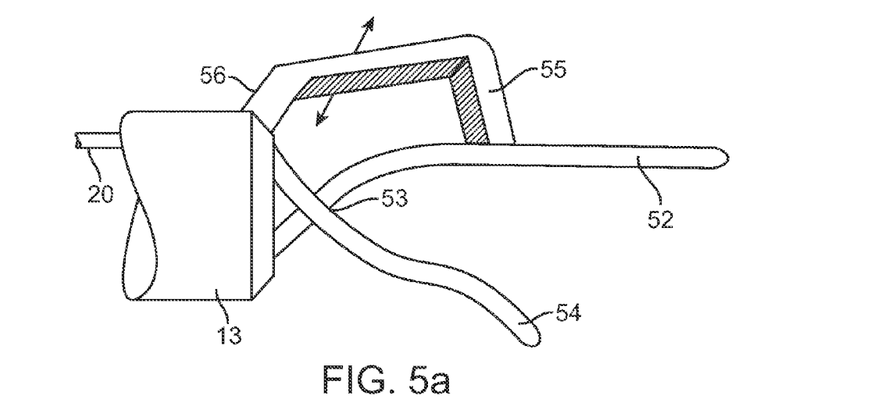
FIGS. 5a and 5b are partial side and top views, respectively, of another embodiment of the present invention.
Figure 5B:
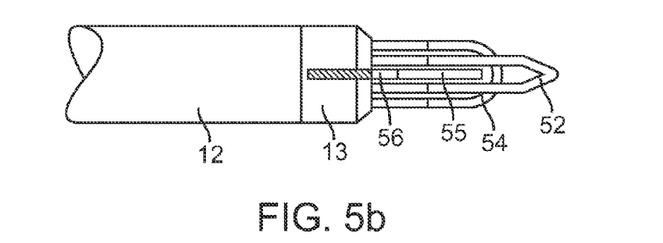

Referring now to FIGS. 5a, 5b, there are shown partial side and top views, respectively, of another embodiment of an end effector according to the present invention in which each of a pair of electrodes 52, 54 for electro cauterizing a tissue structure such as a blood vessel protrude from an insulative hub 13 and retain common polarity in planes substantially aligned with the vessel. One 52 of a pair of wire loops that form the electrodes 52, 54 is assembled through the hub 13 at the distal end of the elongated supporting body 12 to cross through the other 54 of the pair of wire loops in order to form a root or base 53 of converging electrode planes that thereby assure electrical contacts to a vessel of substantially any dimension disposed between the pairs of loop electrodes 52, 54. A hook-shaped blade 55 is disposed to translate longitudinally and laterally within a plane substantially normal to the planes of the electrodes 52, 54 in response to the camming edge 56 of the blade being advanced or retracted relative to a reference surface, in the manner as previously described herein. As illustrated in the partial top view of FIG. 5b, the blade 55 is disposed within, and spaced away from the wire loops that form the electrodes 52, 54. This configuration of the blade 55 and electrodes 52, 54 avoids short circuiting of the electrodes 52, 54 that may be energized by applied bipolar electro cauterizing signals, and also establishes the conductive blade 55 as an additional electrode for alternative grounding or monopolar or bipolar electrocautery operation.

Figure 5C:
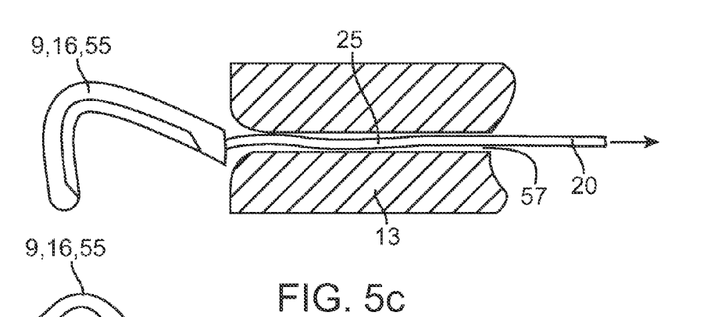
FIGS. 5c and 5d are partial sectional views of a structure for manipulating the transecting blade according to the present invention.
Figure 5D:
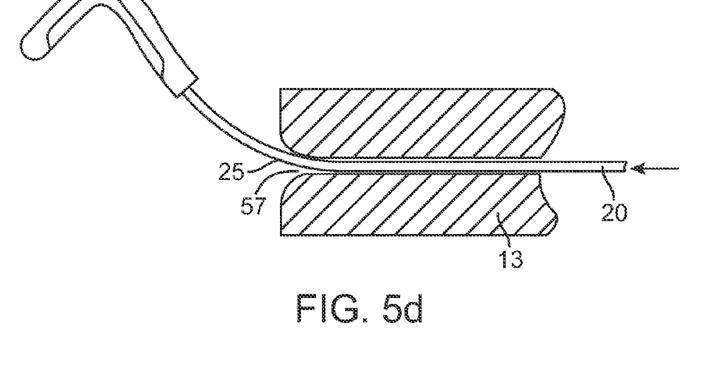

Referring now to the partial side sectional views of FIGS. 5c and 5d, there is shown one embodiment of the present invention for manipulating a cutting blade 9, 16, 55 between open and closed configurations in response to translational movement of the attached actuating rod 20. Specifically, the rod 20 includes a resilient bend 25 that is displaced proximally from the blade 9, 16, 55, and that straightens out to reduce the elevation of the blade as the rod is drawn through a close-fitting lumen 57 within the hub 13 or supporting body 12. The resulting combined downward and retracting movement of the blade 9, 16, 55 greatly facilitates transection of a target tissue structure that is confined beneath the descending and retracting blade.

Figure 5E:
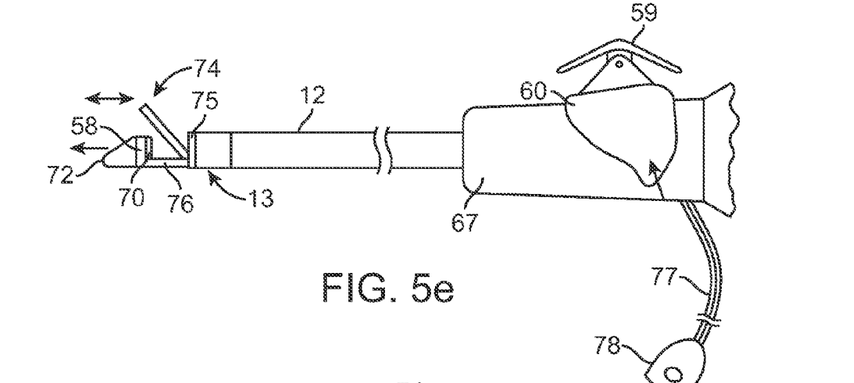
FIGS. 5e, 5f and 5g are, respectively, partial side, end and perspective views of another embodiment of the present invention.
Figure 5F:
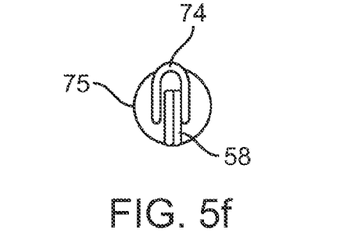
Figure 5G:
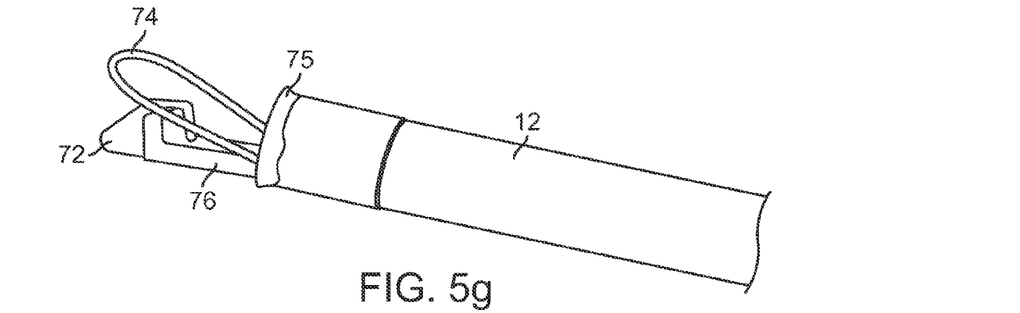

Referring now to the partial side, end and perspective views of FIGS. 5e, 5f, 5g, there is shown another embodiment of an end effector in accordance with the present invention. In this embodiment, the end effector is disposed at the distal end of an elongated support body 12 and includes a blade and electrode structure for electro-cauterizing and transecting tissue structures such as blood vessels. The blade 58 is mounted for translational movement relative to the support body 12 in response to manual manipulation of one or more manual control elements 59, 60 that are mounted on a handle 67 at the proximal end of the support body 12, and that are linked to the blade and electrode structure at the distal end of the body 12. The blade 58 includes a proximal cutting edge 70 that is oriented substantially normally to the direction of translational movement. The blade 58 includes a generally tapered blade guard 72 that protrudes distally from the distal edge of the blade 58 to serve as a manual probe and guide for manipulating the end effector through tissue during positioning of the end effector relative to a target vessel.

A loop electrode 74 surrounds and is spaced from the blade 58, and is disposed within a plane that is skewed to converge proximally with a supporting base 76 of the blade 58. The blade 58 and loop electrode 74 are supported within respective channels within the hub 13 at the distal end of the support body 12. A resilient anvil 75, for example, formed of silicone rubber is disposed against the distal end of the hub 13 to receive the cutting edge 70 at the proximal extent of its translational movement. In this configuration, a tissue structure such as a blood vessel may be confined between the loop electrode 74 and the base 76 of the blade-electrode 58, between the cutting edge 70 and the resilient anvil 75. Bipolar electrical signal supplied to the conductive blade 58 and electrode 74 via electrical conductors 77 within the body 12 and connector 78 thus electrocauterizes the confined tissue prior to being transected by movement of the cutting edge 70 proximally toward the resilient anvil 75. Additionally, the loop electrode 74 may include a resilient bend that can be drawn through its supporting channels within the hub 13, in a manner as previously described herein with reference to FIGS. 1, 5c, 5d, to effect compression of confined tissue against the base 76 of the blade 58. Independent links between the blade 58 and one of the control elements 59, 60, and between the electrode 74 and the other of the control elements 59, 60 greatly facilitate manipulation of the end effector to capture, confine, cauterize and cut a target tissue structure.

Figure 6:
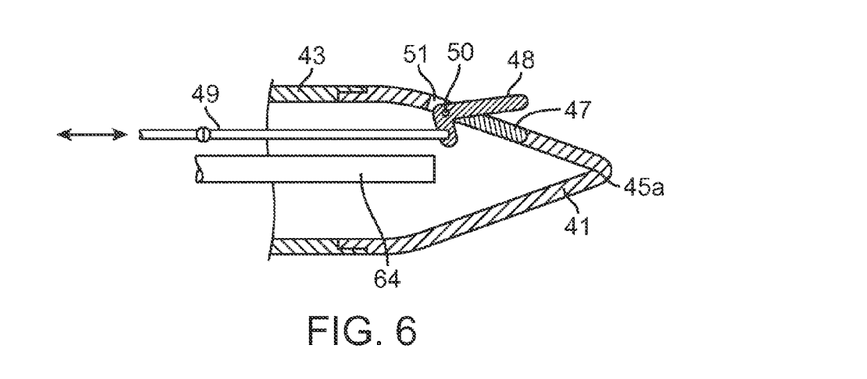
FIG. 6 is a partial sectional view of a tissue-dissecting transparent tip including another embodiment of a tissue transector according to the present invention.

Referring now to the partial sectional view of FIG. 6, there is shown a sectional view of another embodiment of a tissue transector according to the present invention including a section through a transparent tissue-dissecting tip 41 that is attached to the distal end of an endoscopic cannula 43. An endoscope 64 within a lumen in the cannula 43 is substantially aligned with the apex 42 of the tapered tip 41 to establish a field of view through the tip 41 with a minimum of visual distortion and obstruction within the field of view.

In accordance with the illustrated embodiment of the present invention, a tissue transector 47, 48 is disposed within a tapered wall of the tip 41 to facilitate selectively transecting tissue structures such as blood vessels that may be encountered along a course of tissue dissection. Specifically, one cutting blade 47 may be firmly attached to the tip 41, with a cutting edge thereof substantially flush with the tapered outer wall and oriented toward the apex 45a of the tip. Another cutting blade 48 may be pivotally attached to the fixed blade 47 for scissor-like relative movement of the blades about a fixed pivot 50 in response to translational movements of the actuator rod 49 that is linked to the moveable blade 48. A manually actuatable control element (not shown) mounted near a proximal end of the cannula 43 and arranged in conventional manner to translate the actuator rod 49 to implement the scissor-like shearing action of the blades 47, 48 under manual control.

In operation, the pair of blades 47, 48 may be positioned together in closed configuration substantially flush with the outer surface of the tip 41. A slit 51 within the wall of the tip 41 facilitates recessing the blades 47, 48 in the closed configuration to be unobstructive during tissue dissection as the tip is advanced through tissue. Alternatively, an integral recess within the outer wall of the tip may be provided to preserve the sealing properties of the tapered tip 41 relative to the distal end of the cannula 43, and to provide a receptacle within which the blades 47, 48 may be retained in unobstructive closed configuration, until required for selective transection of tissue structures encountered along a tissue-dissection course. Then, a manual actuator (not shown) positioned near a proximal end of the cannula 43 and linked to the rod 49 may translate the rod 49 forward to rotate the blade into the 'open' configuration, as shown. The cannula 43, tip 41 and blades 47, 48 may then be positioned with a tissue structure such as a blood vessel disposed between the blades 47, 48. Tensioning the rod 49 via the manual actuator (not shown) near the proximal end of the cannula 43 thus rotates the blade 48 about the pivot 50 in scissor-like movement to transect the tissue structure disposed between the blades. Of course, the blades 47, 48 may also support electrodes near the cutting edges thereof in conventional manner for use in bipolar electro cauterization of tissue prior to transection.

Figure 7:
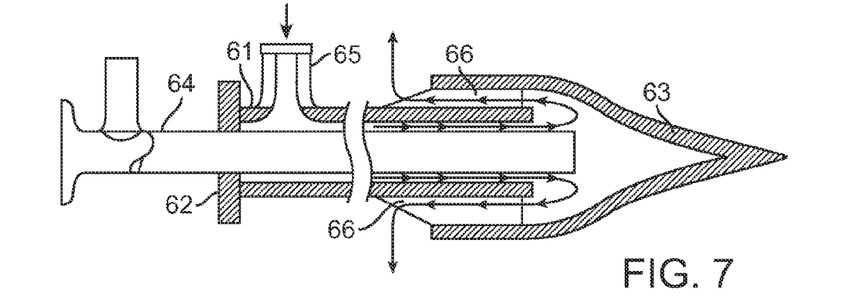
FIG. 7 is a partial sectional view of a transparent tissue-dissecting tip on the distal end of a cannula that includes a lumen therethrough for delivering pressurized fluid in accordance with the present invention.

Referring now to FIG. 7, there is shown a sectional view of an endoscopic cannula 61 having a tissue-dissecting transparent, tapered tip 63 attached to the distal end of the cannula 61, with the apex of the tapered walls substantially aligned with an endoscope 64 disposed within a lumen of the cannula 61. In accordance with the illustrated embodiment of the present invention, the tapered tip 63 is configured to provide both tissue dissection and a convenient gas port for simultaneous insufflation of an anatomical cavity formed in dissected tissue. Specifically, the lumen of the cannula within which the endoscope 64 is fitted (or other lumen) serves as a gas passage forward of the sliding seal 62 along the cannula between a gas-entry port 65 near the proximal end of the cannula 61 and the tip 63 disposed over the distal end of the cannula 61. The tip 63 is spaced away from the cannula 61 by a plural number of radially-extending spacers 66 that are evenly spaced around the perimeter of the cannula 61. The resultant spacing between the distal end of cannula 61 and inner walls of the tip 63 provides an outlet port for gas under pressure to exit from the transporting lumen within the cannula 61. In the illustrated embodiment, stand-off spacers 66 separate the inner walls of the tip 63 from the outer walls of the cannula to establish the gas outlet port. In another embodiment, for example, as illustrated in FIG. 6, a slit 51 through the tapered wall of the tip 41 also serves as an outlet port for gas under pressure to be supplied substantially at the remote surgical site where tissue is being dissected. Positive gas pressure maintained from within a lumen of the cannula 43, 61 and from within the tissue-dissecting tip 41, 63, inhibits incursion of tissue and fluids into the interior of the tip and cannula. And, insufflation gas released in this manner overcomes common problems of trying to insufflate an extended anatomical space in dissected tissue from the location of an access port near the initial incision.

Figures 8, 9:
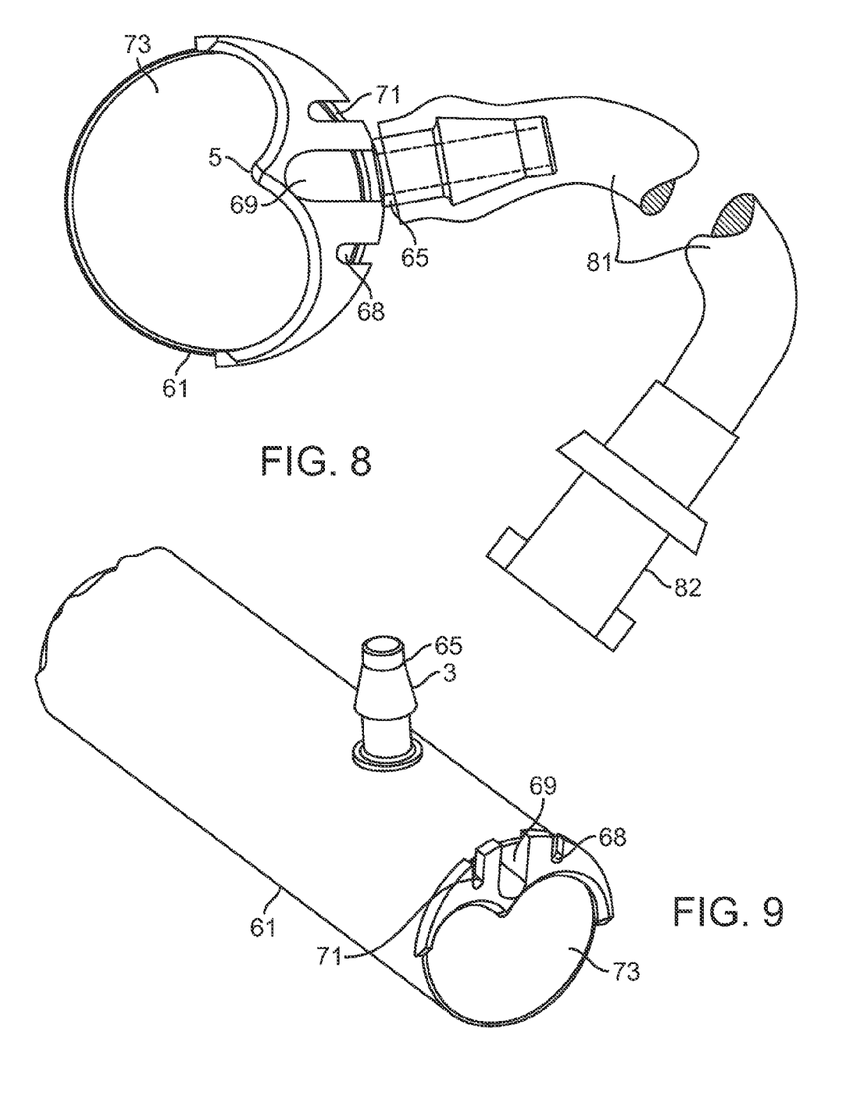
FIG. 8 is a pictorial end view of a cannula including a lumen therethrough for delivery of fluid under pressure to the tissue-dissecting tip.
FIG. 9 is a partial perspective view of the cannula of FIG. 7 illustrating the orientation of multiple lumens within the cannula.

Referring now to the pictorial end view of FIG. 8 and to the partial perspective view of FIG. 9, there is shown a portion of another embodiment of an endoscopic cannula 61 including a gas-inlet port 65 disposed in fluid communication with a lumen 69 that traverses the length of the cannula 61 between proximal and distal ends thereof. The end view of FIG. 8 and the perspective view of FIG. 9 omit for clarity of illustration a proximal-end seal that closes off the proximal end of the lumen 69. Thus, gas supplied under pressure to the lumen 69 through the gas-inlet port 65 is transferred to the remote surgical site near and around the distal end of the cannula for insufflating the anatomical space formed in dissected tissue. Other lumen 68, 71, 73 through the cannula facilitate sliding or rotational movements therein of control rods and surgical instruments, such as an endoscope 64, or transector of FIG. 1, or the like, during endoscopic surgical procedures of a type as previously described herein. Gas such as $CO_2$ under pressure may be conveniently supplied via flexible tubing 81 attached at one end to the gas-inlet port 65 and at an opposite end to a convenient fitting or connector 82 such as a Luer-lock connector. Gas under pressure delivered to the distal end of the cannula in this manner greatly facilitates dilating tissue surrounding an anatomical space formed in tissue near the remote surgical site at which transection of vessels is performed in the manner, for example, as described herein with reference to FIG. 1. In addition, suction can be applied to port 65 to remove fluid from the surgical site.

Figure 10A:
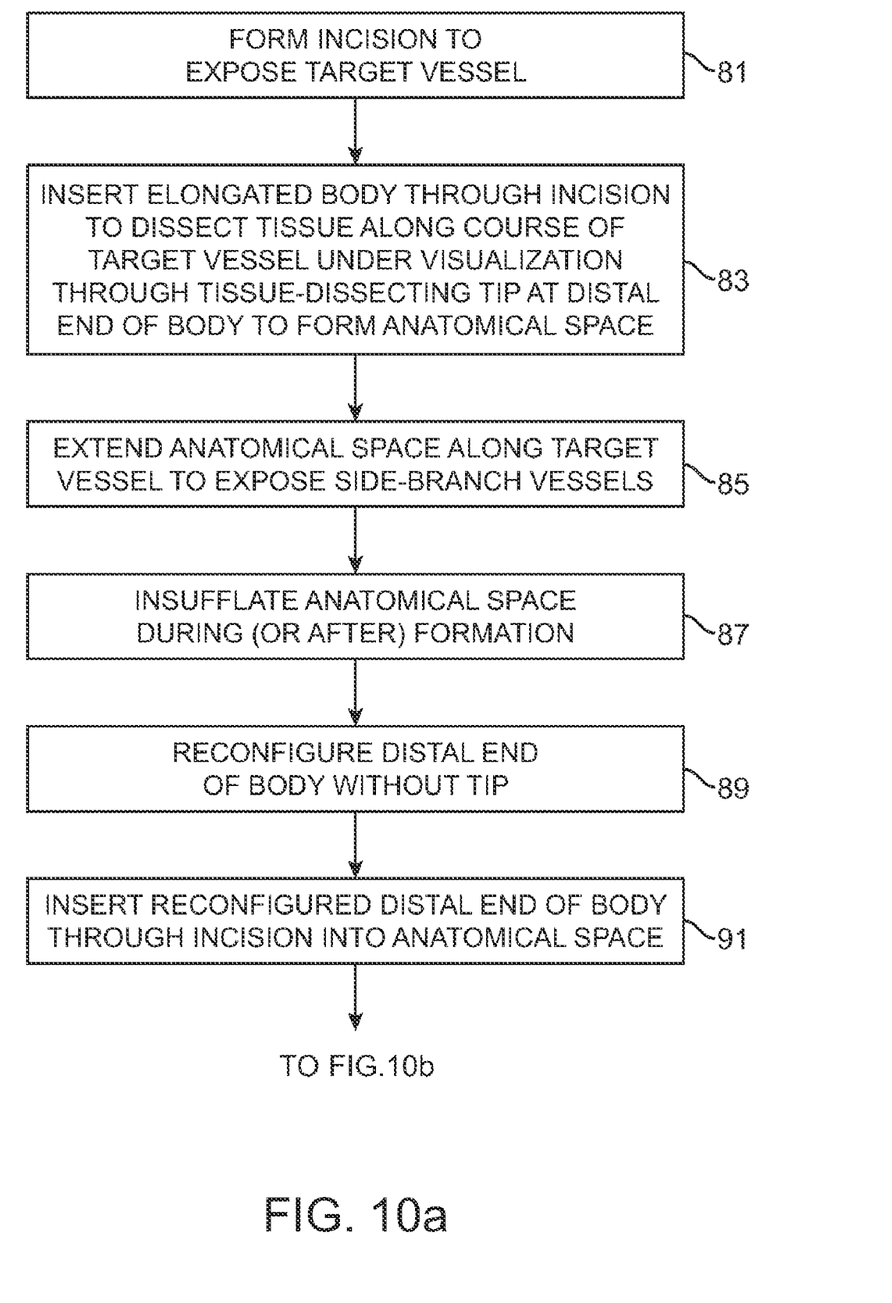
FIGS. 10a and 10b comprise a flow chart illustrating a method embodiment of the present invention.
Figure 10B:
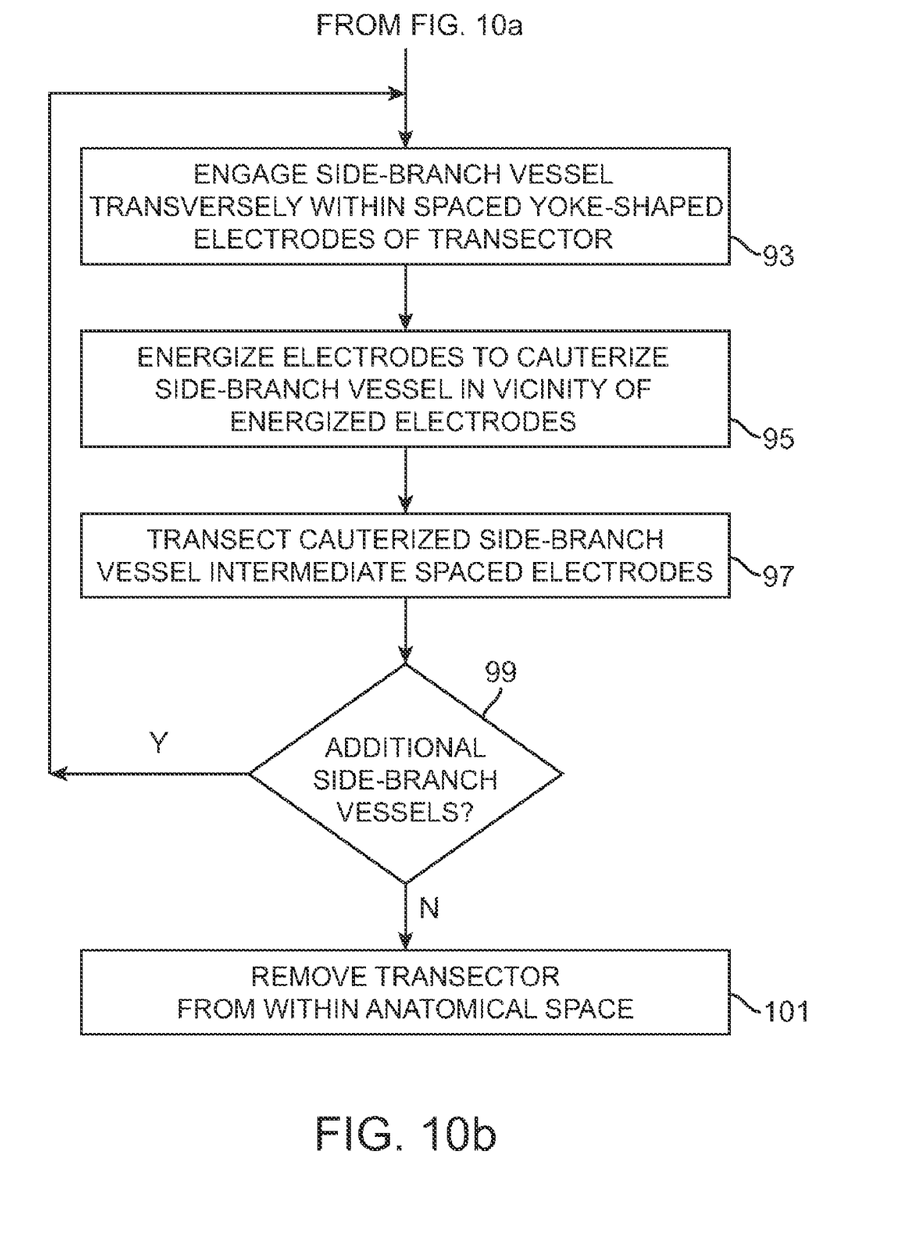

Referring now to the flow chart of FIGS. 10a and 10b, there is shown a method embodiment of the present invention used, for example, to isolate the saphenous vein during a vascular surgical procedure. Specifically, an incision is formed 81 over the saphenous vein to expose the vein and initiate tissue dissection through adherent tissue along the course of the vessel. An elongated cannula, having at least one lumen extending therein substantially between distal and proximal ends and configured with a transparent tissue-dissecting tip disposed over the distal end of the cannula, is inserted through the incision to bluntly dissect tissue 83 away from the saphenous vein and from around side-branch vessel connected to the vein. The tissue dissection is performed under visualization by an endoscope that is positioned within the at least one lumen in the cannula to provide a field of view through the transparent tissue-dissecting tip. A portion of the length of the saphenous vein, and the connected side-branch vessels, are thus exposed and isolated 85 within the anatomical space formed along the vein in the dissected connective tissue. Insufflation of the anatomical space may be performed 87 during or following tissue dissection using gas under pressure that may be delivered in a manner as previously described herein to dilate the tissue surrounding the anatomical space in order to expand the working space around the saphenous vein. The endoscopic cannula is then removed from the anatomical space through the initial incision, and the distal end is reconfigured 89 by removing the tissue-dissecting tip to expose a plural number of lumens that extend within the cannula to the distal end thereof. Alternatively, a cannula having a plural number of lumens extending therein to the distal end thereof, and not requiring reconfiguration by removal of a tissue-dissecting tip from the distal end, may also be used. The cannula thus configured includes a plural number of lumens, for example, as described herein with reference to FIGS. 8 and 9, with an endoscope slidably supported in one lumen, and with a transector such as described herein with reference to FIG. 1 slidably supported within a lumen of the cannula near the endoscope lumen.

The cannula configured with an endoscope and tissue transector extendable through the distal end of the cannula is inserted 91 through the initial incision into the anatomical space along the saphenous vein. A side-branch vessel within the anatomical space is selectively engaged 93 with the transector, for example, with the vessel traversing the slots between yoke-like electrodes, substantially as described herein with reference to FIGS. 2a and 2b. The set of electrodes may be selectively rotated generally about the elongated axis of the supporting body, for example, using a manual actuator as previously described herein with reference to FIGS. 3a, 3b, 3c and 4, in order to orient the yoke-like electrodes to receive the side-branch vessel across the respective slots. The electrodes are bipolarly energized 95 to heat and cauterize the vessel in the region between electrodes, and the cauterized vessel is then severed 97 by the transector blade that is disposed to slice the vessel intermediate the electrodes.

This procedure is used to cauterize and sever each side-branch vessel that is encountered along the course of the portion of the saphenous vein that is isolated within the anatomical space of dissected tissue. After all such side-branch vessels are cauterized and transected 99, the transector may be removed from within the anatomical space 101, and from within the cannula. This facilitates introduction of a ligating and transecting instrument, or instruments, through the cannula to ligate and transect the isolated saphenous vein in conventional manner for removal from the anatomical space.

Therefore, the apparatus and methods for electro cauterizing and transecting tissue in accordance with the present invention facilitate tissue dissection and electro cauterization and transection of tissue at remote surgical sites within tissue being dissected. An anatomical space formed in dissected tissue may be conveniently insufflated at the remote surgical site by delivering gas under pressure to the distal end of a cannula. Endoscopic visualization of tissue dissection at the remote surgical site is greatly improved by providing insufflating gas under pressure through the tissue-dissecting tip. Such remote delivery of insufflating gas to the distal end of the cannula facilitates surgical procedures such as transecting vessels within an anatomical space in dissected tissue.

What is claimed is:

1. An apparatus for treating tissue, comprising:
an elongated body having a distal end and a proximal end;
a first loop member at the distal end of the elongated body;
a second loop member at the distal end of the elongated body;
a cutter moveable relative to the first and second loop members between a first position and a second position, wherein the cutter is configured to cut tissue and to traverse a region between the first and second loop members during movement between the first and second positions; and
an actuator coupled to the cutter for controlling movement of the cutter;
wherein the second loop member is spaced from the first loop member, and intersects an area confined by the first loop member; and
wherein the cutter is positionable to a location that is intermediate the first and second loop members.

2. The apparatus of claim 1, wherein the cutter has a cutting edge that faces towards the proximal end of the elongated body.

3. The apparatus of claim 1, wherein the cutter includes a hook-shaped cutting edge.

4. The apparatus of claim 1, wherein the first loop member confines a first area, the second loop member confines a second area, and the cutter is configured to traverse the first and second areas when moving from the first position to the second position.

5. The apparatus of claim 1, wherein when the cutter is in the second position, the cutter is spaced away from the first and second loop members.

6. The apparatus of claim 1, wherein the first and second loop members are configured to accommodate a vessel that is located between the first and second loop members, and the cutter is configured to cut the vessel while the vessel is located between the first and second loop members.

7. The apparatus of claim 1, wherein the second loop member cooperates with the first loop member to prevent an object from moving proximally.

8. The apparatus of claim 1, wherein the second loop member is fixed in position relative to the first loop member.

9. An apparatus for treating tissue, comprising:
an elongated body having a distal end and a proximal end;
a first loop member at the distal end of the elongated body;
a second loop member at the distal end of the elongated body;
a cutter moveable relative to the first and second loop members between a first position and a second position, wherein the cutter is configured to traverse a region between the first and second loop members during movement between the first and second positions; and
an actuator coupled to the cutter for controlling movement of the cutter;
wherein the second loop member is spaced from the first loop member, and intersects an area confined by the first loop member;
wherein the first loop member has a first outer dimension measured perpendicular to a longitudinal axis of the elongated body, the second loop member has a second outer dimension measured perpendicular to the longitudinal axis of the elongated body, and the second outer dimension is less than the first outer dimension; and wherein the first and second loop members are electrically conductive for receiving electrical signal applied thereto.

10. An apparatus for treating tissue, comprising:
an elongated body having a distal end and a proximal end;
a first loop member at the distal end of the elongated body;
a second loop member at the distal end of the elongated body;
a cutter moveable relative to the first and second loop members between a first position and a second position, wherein the cutter is configured to cut tissue and to traverse a region between the first and second loop members during movement between the first and second positions; and
an actuator coupled to the cutter for controlling movement of the cutter;
wherein the second loop member is fixed in position relative to the first loop member, and cooperates with the first loop member to prevent an object from moving proximally; and
wherein the cutter is positionable to a location that is intermediate the first and second loop members.

11. The apparatus of claim 10, wherein the cutter has a cutting edge that faces towards the proximal end of the elongated body.

12. The apparatus of claim 10, wherein the cutter includes a hook-shaped cutting edge.

13. The apparatus of claim 10, wherein the first loop member confines a first area, the second loop member confines a second area, and the cutter is configured to traverse the first and second areas when moving between the first and second positions.

14. The apparatus of claim 10, wherein when the cutter is at the second position, the cutter is spaced away from the first and second loop members.

15. The apparatus of claim 10, wherein the first and second loop members are configured to accommodate a vessel that is located between the first and second loop members, and the cutter is configured to cut the vessel while the vessel is located between the first and second loop members.

16. The apparatus of claim 10, wherein the first and second loop members are electrically conductive for receiving electrical signal applied thereto.

17. The apparatus of claim 10, wherein the second loop member cooperates with the first loop member to prevent an object from moving proximally past a location, and at least a portion of the cutter is configured to move through the location.

18. The apparatus of claim 10, wherein the second loop member is spaced away from the first loop member.

19. An apparatus for treating tissue, comprising:
an elongated body having a distal end and a proximal end;
a first loop member at the distal end of the elongated body;
a second loop member at the distal end of the elongated body;
a cutter moveable relative to the first and second loop members between a first position and a second position, wherein the cutter is configured to traverse a region between the first and second loop members during movement between the first and second positions; and
an actuator coupled to the cutter for controlling movement of the cutter;
wherein the second loop member is spaced from the first loop member, and cooperates with the first loop member to prevent an object from moving proximally; and
wherein the first loop member has a first outer dimension measured perpendicular to a longitudinal axis of the elongated body, the second loop member has a second outer dimension measured perpendicular to the longitudinal axis of the elongated body, and the second outer dimension is less than the first outer dimension.

20. An apparatus for treating tissue, comprising:
an elongated body having a distal end and a proximal end;
a first loop member at the distal end of the elongated body;
a second loop member at the distal end of the elongated body;
a cutter moveable relative to the first and second loop members between a first position and a second position, wherein the cutter is configured to traverse a region between the first and second loop members during movement between the first and second positions;
a handle; and
an actuator coupled to the cutter for controlling movement of the cutter between the first position and the second position, wherein the actuator is coupled to the handle;
wherein the first loop member extends distally from a first side at the distal end of the elongated body, the second loop member extends from a second side at the distal end of the elongated body that is opposite from the first side; and
wherein the first loop and the second loop intersects at a location that is distal to the distal end of the elongated body.

21. The apparatus of claim 20, wherein the first and second loop member are assembled at the distal end of the elongated body.

22. The apparatus of claim 20, wherein the distal end of the elongated body includes a hub, and wherein the first and second loop member are connected to the hub.

* * * * *